United States Patent
Johnson et al.

[11] Patent Number: 5,922,354
[45] Date of Patent: Jul. 13, 1999

[54] METHODS AND SYSTEM FOR PROCESSING DISPERSIBLE FINE POWDERS

[75] Inventors: Keith A. Johnson; Marc S. Gordon; Shirley W. Lyons, all of Sunnyvale, Calif.

[73] Assignee: Inhale Therapeutic Systems, San Carlos, Calif.

[21] Appl. No.: 08/853,618

[22] Filed: May 9, 1997

Related U.S. Application Data

[62] Division of application No. 08/483,467, Jun. 7, 1995, Pat. No. 5,654,007.

[51] Int. Cl.$^6$ .................................................... A61K 9/14
[52] U.S. Cl. ............................ 424/489; 424/45; 424/46
[58] Field of Search ............................. 424/489, 45, 46; 128/203.12, 203.15

[56] References Cited

U.S. PATENT DOCUMENTS

| | | |
|---|---|---|
| 4,137,914 | 2/1979 | Wetterlin . |
| 4,174,712 | 11/1979 | Morén et al. . |
| 4,524,769 | 6/1985 | Wetterlin . |
| 4,667,668 | 5/1987 | Wetterlin . |
| 4,897,267 | 1/1990 | Bontemps . |
| 5,186,166 | 2/1993 | Riggs et al. .................. 128/203.15 |
| 5,376,359 | 12/1994 | Johnson . |
| 5,531,219 | 7/1996 | Rosenberg .................. 128/203.12 |
| 5,639,441 | 6/1997 | Sievers et al. .................. 424/9.3 |

FOREIGN PATENT DOCUMENTS

| | | |
|---|---|---|
| 0 237 507 A1 | 9/1987 | European Pat. Off. . |
| 0 260 241 A1 | 3/1988 | European Pat. Off. . |
| 0 508 969 A1 | 10/1992 | European Pat. Off. . |
| 1515017 | 5/1969 | United Kingdom . |
| 2156783 | 10/1985 | United Kingdom . |
| WO 90/07351 | 7/1990 | WIPO . |
| WO 93/21980 | 11/1993 | WIPO . |
| WO 94/13271 | 6/1994 | WIPO . |
| WO 95/00127 | 1/1995 | WIPO . |

OTHER PUBLICATIONS

S.P. Newman, et al., *Eur Respir J.*, 1989, 2:247–252.
S. Pedersen, *Archives of Disease in Childhood*, 1986, 61:11–14.
Dr. Gabrie M.H. Meesters, "Not so dusty," Background to Biotechnology, (Part 38).
Product brochure: *Fine–Granulation Technology*, LCI Corporation, Processing Div., Charlotte, North Carolina.
Product brochure: *Sizing Up the Agglomeration Process*, BEPEX Corp., Minneapolis, Minnesota, ©1992.
E.M. Phillips et al., (Abstract PT 1660), *Pharm. Res.*, 1995, 11(10), p. S–158.

*Primary Examiner*—Thurman K. Page
*Assistant Examiner*—William E. Benston, Jr.
*Attorney, Agent, or Firm*—Townsend and Townsend and Crew

[57] ABSTRACT

The invention provides an agglomerate composition composed of units of aggregated fine particles and methods for its manufacture and use. The agglomerate composition units are composed of fine particles having a mean particle size in the range of 1 $\mu$m to 5 $\mu$m, and usually includes a medicament powder. The agglomerate units have a mean size in the range from 200 $\mu$m to 500 $\mu$m and have a friability index in the range from about 10 to 60.

14 Claims, 1 Drawing Sheet

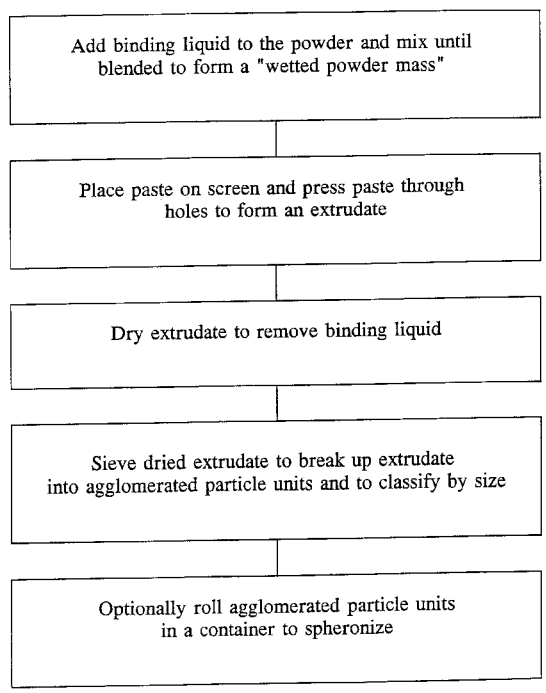

FIG. 1

```
┌─────────────────────────────────────────────────────────┐
│  Add binding liquid to the powder and mix until         │
│  blended to form a "wetted powder mass"                 │
└─────────────────────────────────────────────────────────┘
                            │
┌─────────────────────────────────────────────────────────┐
│  Place paste on screen and press paste through          │
│  holes to form an extrudate                             │
└─────────────────────────────────────────────────────────┘
                            │
┌─────────────────────────────────────────────────────────┐
│  Dry extrudate to remove binding liquid                 │
└─────────────────────────────────────────────────────────┘
                            │
┌─────────────────────────────────────────────────────────┐
│  Sieve dried extrudate to break up extrudate            │
│  into agglomerated particle units and to classify by size│
└─────────────────────────────────────────────────────────┘
                            │
┌─────────────────────────────────────────────────────────┐
│  Optionally roll agglomerated particle units            │
│  in a container to spheronize                           │
└─────────────────────────────────────────────────────────┘
```

METHODS AND SYSTEM FOR PROCESSING DISPERSIBLE FINE POWDERS

This is a division of application No. 08/483,467 filed Jun. 7, 1995, now U.S. Pat. No. 5,654,007, the disclosure of which is incorporated by reference.

BACKGROUND OF THE INVENTION

1. Field of the Invention

The present invention relates generally to a system and methods for processing fine dispensable powders. More particularly, the present invention relates to a system and methods for forming fine powdered medicaments into agglomerates for easier processing, where the agglomerates are readily broken back down to the fine powder when needed for pulmonary delivery or other uses benefitting from fine powders.

Effective delivery to a patient is a critical aspect of any successful drug therapy. Various routes of delivery exist, and each has its own advantages and disadvantages. Oral drug delivery of tablets, capsules, elixirs, and the like, is perhaps the most convenient method, but many drugs are degraded in the digestive tract before they can be absorbed. Such degradation is a particular problem with modern protein drugs which are rapidly degraded by proteolytic enzymes in the digestive tract. Subcutaneous injection is frequently an effective route for systemic drug delivery, including the delivery of proteins, but enjoys a low patient acceptance. Since the need to inject drugs on a frequent schedule, such as insulin one or more times a day, can be a source of poor patient compliance, a variety of alternative routes of administration have been developed, including transdermal, intranasal, intrarectal, intravaginal, and pulmonary delivery.

Of particular interest to the present invention are pulmonary drug delivery procedures which rely on inhalation of a drug dispersion or aerosol by the patient so that the active drug within the dispersion can reach the distal (alveolar) regions of the lung. It has been found that certain drugs are readily absorbed through the alveolar region directly into blood circulation. Pulmonary delivery is particularly promising for the delivery of proteins and polypeptides which are difficult to deliver by other routes of administration. Such pulmonary delivery can be effective both for systemic delivery and for localized delivery to treat diseases of the lungs.

Pulmonary drug delivery (including both systemic and local) can itself be achieved by different approaches, including liquid nebulizers, metered dose inhalers (MDI's) and dry powder dispersion devices. Dry powder dispersion devices are particularly promising for delivering protein and polypeptide drugs which may be readily formulated as dry powders. Many otherwise labile proteins and polypeptides may be stably stored as lyophilized or spray-dried powders by themselves or in combination with suitable powder carriers.

The ability to deliver proteins and polypeptides as dry powders, however, is problematic in certain respects. The dosage of many protein and polypeptide drugs is often critical so it is necessary that any dry powder delivery system be able to accurately, and precisely (repeatably) deliver the intended amount of drug. Moreover, many proteins and polypeptides are quite expensive, typically being many times more costly than conventional drugs on a per-dose basis. Thus, the ability to efficiently deliver the dry powders to the target region of the lung with a minimal loss of drug is critical.

An exemplary dry powder dispersion device for efficiently delivering dry powder medicaments to the lungs is described in copending U.S. patent application Ser. No. 08/309,691, filed Sep. 21, 1994 (attorney docket no. 15225–5), the disclosure of which is herein incorporated by reference. Such a dispersion device is constructed to receive the powdered medicament in a receptacle having a puncturable lid or other access surface. The receptacle is placed in the device, and a feed tube is penetrated into the lid of the receptacle to provide access to the powdered medicament therein. A high velocity gas stream is then flowed past a portion of the tube, such as an outlet end, to draw powder from the receptacle, through the tube, and into the flowing gas stream to form an aerosol for inhalation by the patient.

Of particular interest to the present invention are the physical characteristics of the fine powders to be delivered by such apparatus, and particularly, the flowability of the fine powders. Most fine powders have poor flowability which can often be problematic when attempting to process, e.g. move and meter, the powders. For example, in the case of fine powder medicaments, poor flowability increases the time and/or reduces the accuracy of filling the receptacles with unit doses of the powdered medicaments for subsequent use in a powder inhaler. Therefore, a significant improvement in the powder flow will increase the probability for success of filling processes.

To improve the flowability of fine powder medicaments, some have proposed the use of a blending process where the powdered medicaments are combined or blended with larger carrier particles, such as coarse (i.e greater than 25 $\mu$m) lactose particles, which have easier handling and flowability characteristics. Use of a carrier, however, presents a variety of problems including dilution of the drug, requiring a larger dispersion volume for a given drug dosage, and the potential for poor content uniformity of the blend.

Another proposed process for improving flowability is to increase the size of small particles by agglomeration where the fine powders are combined into larger-sized aggregated units. Such aggregated units can be formed by a variety of processes including low shear granulation, high shear granulation, roller compaction or dry granulation, and extrusion. One particular concern with the formulation of inhalation powders into aggregated units is the resulting friability of the aggregated units, i.e. the ability of the aggregated units to be broken down to the fine powder. If the aggregated units are not sufficiently friable, they cannot be sufficiently broken down by an inhaler when used for pulmonary delivery. Another concern with the formulation of inhalation powders into aggregated units is their resulting size. The aggregated units should have a narrow size distribution so that they may be utilized in existing inhalation devices. For example, if the aggregated units are too large, they can become trapped within the holding receptacle and will not be delivered to the lungs.

The extrusion process is advantageous over other agglomeration processes in that it allows for the rapid formation of aggregated units in a specific size range using low pressures. In the extrusion process, the fine powder is wetted with a liquid, referred to as a binding liquid, and then forced through a screen to form an extrudate. The extrudate is then dried and sieved to break up the extrudate into the aggregated units. Typically, water, ethanol, glycerin, iso-propanol, or methanol are used as the binding liquid. One particular drawback to the use of such liquids is that a significant portion of proteins are susceptible to denaturation following exposure to alkanols. Alkanols and water can also solubilize excipients in the powder, such as carbohydrates and buffer salts. Excipients solubilized by the binding liquid can lead to the formation of strong crystalline bridges between particles, thereby strengthening the aggregated units and making them more difficult to disperse.

Hence, for these and other reasons, it would be desirable to provide improved systems and methods for agglomerating fine powders into aggregated units that would overcome or greatly reduce such problems. The systems and methods should allow for the aggregated units to be produced with a narrow size distribution and to have an appropriate level of friability, i.e. neither too high nor too low, so that the aggregated units can be used with existing dry power inhalers which require the break up of the aggregated units prior to inhalation. In one aspect, it would further be desirable to provide systems and methods for producing agglomerate powders with a binding liquid that does not interact with the hydrophilic or lipophilic components of the powder.

2. Description of the Background Art

Dry powder dispersion devices for medicaments are described in a variety of patent documents, including U.S. Pat. Nos. 4,137,914; 4,174,712; 4,524,769; 4,667,688; U.K. Patent Application No. 2,156,738; European Patent Application No. 87850060.2; and PCT Application Nos. PCT/SE93/00389; PCT/SE93/01053; and PCT/DK90/00005.

A process for providing water-soluble micronized substances is described in European Patent Application No. 92850062.8.

A system for administration of liposomes to mammals is described in European Patent Application No. 87850273.1.

U.S. Pat. No. 5,376,359 describes a method for making a stabilized aerosol drug formulation.

British Patent No. 1,151,017 describes a process for producing finely divided metal powders.

A variety of publications describe various powder inhalers including S. P. Newman et al., Deposition and clinical efficacy of turbutaline sulphate from Turbuhaler, a new multi-dose powder inhaler, *Eur Respir J,* 1989, 2:247–252; S. Pedersen, How to use a Rotahaler, *Arch Dis Child,* 1986, 61:11–14.

Dr. Gabrie M. H. Meesters, Not so dusty, describes market demand for free flowing powders through agglomeration.

Product brochures Fine-granulation technology, LCI Corporation, Processing Division, Charlotte, N.C. and Agglomeration: sizing up the agglomeration process, BEPEX Corporation, Minneapolis, Minn., ®1992, describe processes for producing agglomerated particles.

E. M. Phillips et al., Formulation Development of spray Dried Powders for Inhalation (Abstract), *Pharm. Res.,* 11(10), S-158, 1995 describes the aerosolization of spray dried powders.

SUMMARY OF THE INVENTION

The invention provides an agglomerate composition composed of aggregated units of fine particles along with methods for its manufacture and use. By the term "aggregated unit", it is meant that a number of fine particles are bound together into a single geometric configuration. A plurality of such units are referred to as aggregated units. The aggregated units are unconnected to each other and collectively form the agglomerate composition. The aggregated units will usually have a mean size in the range from 50 $\mu$m to 600 $\mu$m, preferably between about 150 $\mu$m and 500 $\mu$m, and more preferably between 200 $\mu$m to 500 $\mu$m, and are composed of fine particles having a mean particle size in the range from 1 $\mu$m to 5 $\mu$m. Forming the fine particles into aggregated units in this manner improves the flowability of the fine particles, thereby allowing for easier processing and handling of the particles. The agglomerate composition is formed in such a way that the aggregated units have a friability index (as described hereinafter) in the range from about 10 to 60. Preferably, the particles comprise a medicament powder useful in pulmonary drug delivery procedures where the medicament powder is inhaled by a patient so that the active drug in the powder can reach the distal regions of the lung. Preferable medicament powders include those having medicaments such as proteins, nucleic acids, carbohydrates, buffer salts, peptides, other biomolecules, small molecule drugs, and the like. By forming the medicament powder into an agglomerate composition, the medicament can more easily be moved and metered prior to inhalation while also having the ability to easily be broken down to the fine particles when needed for delivery to the patient's lungs.

In one aspect of the invention, an agglomerate composition is provided which is composed of fine particles formed into aggregated units, with the fine particles having a mean particle size in the range from 1 $\mu$m to 5 $\mu$m. The aggregated units have a mean size in the range from 200 $\mu$m to 500 $\mu$m and are formed by employing a nonaqueous solvent binding liquid. The use of a nonaqueous solvent is desirable in that the carbohydrates and proteins of the medicament powders are typically poorly soluble in such a solvent. Poor solubility is desirable so that the formation of crystalline bridges between particles will be minimized. The minimization of crystalline bridges will allow the aggregated units to be broken down into the fine powder when needed. Many nonaqueous solvents also have a low boiling point, and therefore a high vapor pressure, so that they may be readily removed from the aggregated units. Additionally, most nonaqueous solvents have a low surface tension and therefore form weak bonds between particles, allowing the agglomerated units to be broken down into the fine particles when needed. Further, some nonaqueous solvents will not denature proteins. Preferable nonaqueous solvents include, but are not limited to toluene, xylene, benzene, acetone, hexane, octane, chloroform, methylene chloride, and fluorocarbons.

Use of a fluorocarbon liquid in forming the aggregated units is particularly preferable because the fluorocarbon liquid will not dissolve lipophilic and hydrophilic compounds. Further, the fluorocarbon liquid has a low surface tension which forms a relatively weak bond between the fine particles of the aggregated units so that the aggregated units can easily be broken down to the fine particles when needed. Fluorocarbon liquids further have a high vapor pressure and are therefore easy to remove from the particles during formation of the aggregated units. Fluorocarbon liquids are also biocompatible with many pharmaceutical formulations. Preferable fluorocarbon liquids include but are not limited to perfluorodecalin and perfluorooctyl bromide.

In another aspect of the invention, a receptacle is provided having a sealed internal volume and a penetrable wall portion. Within the sealed internal volume is an amount of an agglomerate composition as previously described. The amount of agglomerate composition is preferably a unit dosage of a medicament. When filled with the agglomerate medicament, the receptacle is useful in an inhalation device using a gas stream to withdraw the agglomerate composition from the receptacle where the aggregate units are broken down to the fine particles for delivery to the patient's lungs.

According to one method of the invention, such a receptacle is provided with a fine powder agglomerate composition where the fine powder is characterized by a mean particle size in the range from 1 μm to 5 μm. The fine powder is formed into aggregated units having a mean size in the range from 50 μm to 600 μm, preferably between about 150 μm and 500 μm, and most preferably between 200 μm to 500 μm. The agglomerate composition from the receptacle is extracted in a gas stream for delivery to a patient's lungs, with the gas stream having sufficient disruptive force to break down the aggregated units substantially completely, i.e., at least 30%, preferably at least 50%, and most preferably at least 70%, to the fine particles. In one particular aspect, the agglomerate composition is extracted by flowing the gas stream past a tube inserted into the receptacle.

In one aspect, the gas stream is flowed at a sonic velocity to provide sufficient disruptive force. In another aspect, usually at least 55 percent by weight, preferably at least 70 percent by weight, and more preferably at least 90 percent by weight of the agglomerate composition initially present in the receptacle is extracted into the airstream for delivery to the patient's lungs.

The invention provides a method for agglomerating fine particles. According to the method, a powder of fine particles is combined with a binding liquid to produce a wetted mass, such as a granulation or a paste. The wetted mass is then divided into small volumes which are dried to remove the binding liquid and to produce dry powder agglomerate units having a first size distribution. The dry powder agglomerate units are then adjusted to have a second size distribution characterized by a friability index in the range from about 10 to 60.

The fine particles preferably have a mean particle size in the range from 1 μm to 5 μm. When adjusted to the second size distribution, the dry powder agglomerate units preferably have a mean size in the range from 50 μm to 600 μm, preferably between about 150 μm and 500 μm, and most preferably between 200 μm to 500 μm. The aggregated units will be formed such that substantially all, i.e. about 90% or more, fall within a narrow size distribution, i.e. within about ±250 μm, more preferably within about ±150 μm, and most preferably within about ±100 μm.

In an exemplary aspect, the paste or granulation is divided into small volumes by extruding the paste or granulation through a screen having holes in the range from 40 μm to 650 μm, and more preferably in the range from 150 μm to 500 μm. Preferably, the holes are circular in geometry, thereby producing elongate cylindrical portions of extrudate. The extrudate is preferably dried at a temperature in the range from 15° C. to 40° C. Preferable environments for drying the extrudate include the use of forced convection with dry air or by placing the extrudate in a vacuum. To adjust the agglomerate units to the second size distribution, the dry powder agglomerate units are preferably sieved. Optionally, the dry powder agglomerate units can further be adjusted to have a spherical geometry, often referred to as spheronization. In one aspect, the agglomerate units are spheronized by rolling the agglomerate units in a container.

In another exemplary aspect, the binding liquid is preferably a nonaqueous solvent, more preferably a fluorocarbon, and the fine particles will preferably comprise a medicament powder. The amount of binding liquid added to the medicament powder is preferably based on the surface area of the powder. Preferably, the fluorocarbon liquid is perfluorodecalin, and the fine particles have a mean particle size in the range from 1 μm to 5 μm. With such a configuration, the amount of fluorocarbon added is preferably in the range from 0.5 gram to 5 gram per gram of fine particles.

BRIEF DESCRIPTION OF THE DRAWINGS

FIG. 1 is flow chart illustrating an exemplary method for agglomerating fine particles according to the present invention.

DETAILED DESCRIPTION OF THE SPECIFIC EMBODIMENTS

The invention provides an agglomerate composition composed of aggregated fine particle units, along with methods for its manufacture and use. Although useful in a wide variety of applications, the agglomerate composition will find its greatest use with pulmonary drug delivery procedures which rely on the inhalation of a drug dispersion by a patient so that the active drug within the dispersion can reach the alveolar regions of the lung.

The agglomerate composition is provided to improve the ability to handle and process the fine particles. By bonding the fine particles together to form aggregated units, flowability of the particles is improved. Improved flowability is desirable in that it allows for easier transfer and metering of the particles. The aggregated units are formed by binding the fine particles together with a bond sufficiently strong to hold the fine particles together during handling and processing yet weak enough so that the aggregated units can be broken down to the fine particles when needed, usually upon dispersion into an aerosol for delivery of the particles to the lungs.

The fine particles employed in the present invention have a size that is small enough to effectively be delivered to the alveolar regions of the lung when inhaled by a patient. Such particles are very fine, usually having a mean size in the range from 1 μm to 5 μm. Such small sizes make handling and metering of the particles difficult. For instance, transfer of the particles often occurs through a funnel. When traveling through the funnel, the particles often clump together and clog the funnel. By forming the particles into agglomerates, flowability is improved allowing for easier movement of the particles.

In a preferred aspect of the invention, the particles comprise a medicament powder. Exemplary medicament powders include powders made of proteins, nucleic acids, peptides, buffer salts, other biomolecules, and the like, and can include carrier materials such as carbohydrates. One particularly preferable medicament powder is insulin which has been shown to be effective when delivered in powdered form.

Aggregated units of the invention preferably have a mean size in the range from 50 μm to 600 μm, more preferably between about 150 μm and 500 μm, and most preferably between 200 μm to 500 μm. Such a size allows for improved handling and flowability of the powder. As described in greater detail hereinafter, such a size is also small enough for the aggregated units to be effective when used in inhalation devices. To further improve the flowability, the aggregated units can optionally be provided with a spherical geometry. When forming the aggregated units, it is desirable to have substantially all, i.e. about 90% or more, fall within a narrow size distribution, i.e. within about ±250 μm, more preferably within about ±150 μm, and most preferably within about ±100 μm. Such a narrow size distribution makes it easier for the aggregated units to be dispersed within an inhaler.

To bind the fine particles into aggregated units, a binding liquid is employed. The binding liquid is added to the particles, with the surface tension of the liquid holding the particles together. When wetted, a granulation or paste is formed allowing the particles to be formed or molded into an aggregated unit having the desired shape and size. The aggregated unit is then dried to remove the binding liquid and to leave the aggregated unit in the desired shape.

The resulting aggregated unit is held together by a series of bonds that are strong enough to hold the aggregated unit together during normal handling and metering procedures. At the same time, the bonds are weak enough so that the aggregated unit can be broken down to the fine particles when needed, i.e., the aggregated units have an appropriate level of friability. Sufficient friability is particularly important in inhalation devices where it is desirable to have the aggregated units broken down to the fine particles when delivered to the lungs. As used herein, the friability of the aggregated units is determined by the following friability test. The friability test measures the attrition of the aggregated units after shaking the units through a stack of sieves, using a specific frequency and amplitude, for a specified time.

The sieve stack includes seven vertically arranged screens. Each screen is 3 inches in diameter and is separated from an adjacent screen by 1.25 inches. In order from top to bottom, the screen sizes are: 1000 $\mu$m, 500 $\mu$m, 425 $\mu$m, 355 $\mu$m, 300 $\mu$m, 250 $\mu$m, and 150 $\mu$m. Below the 150 $\mu$m screen is a collection pan. To test the friability, an amount of the aggregated units in the range from about 0.4 g to 0.5 g is weighed to give a beginning weight $W_1$. The weighed aggregated units are then placed on the 1000 $\mu$m screen, and the entire stack is vibrated for 20 minutes with an amplitude of approximately 1 cm and at a frequency of approximately 5 Hz. After the 20 minutes, the vibration is ceased, and the aggregated units which have not been broken down to the fine particles are collected and weighed to give a weight $W_2$. The aggregated units can easily be collected by pouring them from the sieve stack since the fine powder will have either been collected in the pan or will coat the screens. The ending weight $W_2$ is then divided by the beginning weight $W_1$ to give a percentage of aggregated units that have not been broken down to the fine particles. The particular numerical values of the percentages are referred to as the friability index. For example, if 50 percent of the aggregated units were broken down using the friability test, the friability index for such aggregated units would be 50. A preferable friability index for pulmonary powder inhalers as described herein is in the range from about 10 to 60.

In addition to holding the agglomerate together, the binding liquid also reduces the level of dust, or loss of product, when applied to the powder. In this way, waste of the powdered medicaments is reduced.

Exemplary binding liquids include nonaqueous solvents, preferably fluorocarbon liquid, and more preferably perfluorodecalin or perfluorooctyl bromide, with the most preferred being perfluorodecalin. Other exemplary nonaqueous solvents include toluene, xylene, benzene, acetone, hexane, octane, chloroform, and methylene chloride. The use of a nonaqueous solvent is desirable in that carbohydrates and proteins are usually poorly soluble in them, thereby minimizing the formation of crystalline bridges between particles. Further, most nonaqueous solvents have a low surface tension which allows the agglomerates to more easily be broken down to the fine particles when needed. Moreover, many nonaqueous solvents have a low boiling point, and hence high vapor pressure, allowing them to be easily removed from the agglomerates. In a further aspect, some nonaqueous solvents will not denature proteins.

The use of fluorocarbon liquids are particularly preferable in that they are hydrophobic and do not dissolve carbohydrates or proteins. Fluorocarbon liquids are also lipophobic and do not interact with the proteins. Further, fluorocarbon liquids have a low surface tension and therefore form weak bonds between the particles so that the desired level of friability for the agglomerates can be obtained. Fluorocarbon liquids also have a high vapor pressure and are therefore easy to remove from the agglomerates. In a further advantage, fluorocarbon liquids do not contain fluorine and are therefore ozone-friendly. In a further aspect, fluorocarbon liquids are biocompatible with most pharmaceutical formulations, such as blood substitutes and imaging aids. Suitable fluorocarbon liquids are commercially available from a variety of commercial suppliers including PCR, Inc. (Gainesville, Fla.), Sigma Chemical Company (St. Louis, Mo.), and Aldrich Chemical Company, Inc. (Milwaukee, Wis.).

Delivery of powdered medicaments to the lungs is usually accomplished by use of an inhalation device which fluidizes the powdered medicament in an airstream which can then be inhaled by the patient to deliver the medicament to the patient's lungs. Hence, before pulmonary delivery, the aggregated units must be broken down to the powdered medicament. By providing the aggregated units with the desired friability, the aggregated units can be broken down into powdered form within the inhaler. In this way, the powdered medicaments can remain in agglomerate form for measurement and handling until needed for pulmonary delivery by the inhaler.

The aggregated units are usually delivered to the inhaler in unit dosage receptacles, commonly referred to as blister packs or cartridges. The manufacture of blister packs is well-known in the pharmaceutical packaging art and need not be described further. To extract the aggregated units from the receptacle, a wall of the receptacle is pierced when the receptacle is held within the inhaler. An exemplary inhaler is described in U.S. patent application Ser. No. 08/309,691, filed Sep. 21, 1994, the disclosure of which has previously been incorporated herein by reference. With the receptacle opened, the aggregated units are extracted into a gas stream having sufficient disruptive force to break down the aggregated units to the fine particles. When having the desired friability, the aggregated units can be broken down to the fine particles when the gas stream is flowed at a velocity sufficient to provide adequate shear forces needed to break down the aggregated units. Preferably, such a gas stream is flowed at a sonic velocity to provide the sufficient disruptive force. Optionally, when the aggregated units are placed into the blister packs, the blister packs can be subjected to vibratory energy. Subjecting the aggregated units to vibratory energy when within the blister packs assists in breaking down the aggregated units to the fine particles before they are extracted by the inhaler. In this way, the aggregated units can be produced with a smaller friability index and still be useful in pulmonary delivery procedures.

The aggregated units should be broken down substantially completely, i.e., at least 30%, preferably at least 50%, and most preferably at least 70% of the aggregated units that are extracted from the receptacle being broken down to 1 $\mu$m to 5 $\mu$m, before being inhaled by the patient. Such decomposition to the fine particles is realizable when the aggregated units have a friability index in the range from about 10 to 60. When having the desired mean size range of 200 $\mu$m to 500 $\mu$m, substantial complete removal of the aggregated units (usually at least 55 percent, and preferably at least 70 percent, and more preferably at least 90 percent by weight) from the interior of the receptacle is obtainable. Formation of aggregated units having a mean size range of greater than about 600 μm reduces the percentage of powder removed from the receptacle by the airstream because the larger aggregated units tend to become trapped behind the penetrated walls of the receptacle.

Referring to FIG. 1, an exemplary method for agglomerating fine particles will be described. According to the method, a binding liquid is added to a powder of fine particles to produce a wetted powder mass. Preferably, the fine particles are a medicament powder having a mean particle size in the range from 1 μm to 5 μm, and the binding liquid is a nonaqueous solvent, preferably fluorocarbon, and more preferably perfluorodecalin. The granulation or paste is mixed to ensure uniform distribution of the binding liquid. After mixing, the granulation or paste is extruded to divide the granulation or paste into smaller volumes. The granulation or paste is preferably extruded by pressing the granulation or paste through a screen having holes in the range from 40 μm to 650 μm, preferably at about 150 μm to 500 μm, and more preferably at about 250 μm to 400 μm. Extrusion screens having less than 500 μm holes can be provided by mechanical punching, electrical discharge, or laser drilling a thin sheet of metal as is known in the art. The holes in the extrusion screen are preferably circular in geometry so that elongate cylindrical portions of extrudate are formed when the paste is pressed through the screen.

The extrudate is then dried to remove the binding liquid from the extrudate. Drying can be accomplished in a variety of ways including placing the extrudate in a vacuum chamber having a vacuum in the range from 250 mmHg to 650 mmHg, and with a temperature within the chamber being in the range from 15° C. to 40° C. or by forced convection with dry air having a temperature in the range from about 15° C. to 40° C. After drying, the extrudate is sieved to break up the extrudate into agglomerated particle units and to classify the agglomerated particle units by size. Preferably, the sieve will have holes sized in the range from 150 μm to 1000 μm and will be vibrated either at a frequency in the range from 0.5 Hz to 10 Hz and at an amplitude in the range from about 5 mm to 50 mm or, alternatively, vibration may be accomplished by a tapping action combined with lateral and/or tiling motions or circular rotation.

The resulting agglomerated particle units preferably have a mean size in the range from 50 μm to 600 μm, more preferably between about 150 μm and 500 μm, and most preferably between 200 μm to 500 μm. If needed, the agglomerated particle units can be subjected to a spheronization process to spheronize the agglomerated units. Spheronization is often desirable because it can improve the flowability of the agglomerated particle units. Spheronization can occur by rolling the agglomerated particle units, such as in a metal or a glass container.

The amount of binding liquid added to the medicament powder is generally based on the surface area of the fine particles, as illustrated in the following examples. When using fluorocarbon liquid as the binding agent along with fine particles having a mean particle size in the range from 1 μm to 5 μm, the amount of fluorocarbon added is preferably in the range from 0.5 gram to 5 gram per gram of fine particles.

The present invention is explained in greater detail in the following non-limiting examples.

EXAMPLES

Fine powders having a weight of about 0.5 g to 10 g were combined with a nonaqueous solvent to form a wetted mass. The wetted mass was then extruded through a screen. The resulting extrudate was then dried (by forced convection or in a vacuum) at room temperature for at least one hour to remove the nonaqueous solvent. The dried extrudate was then sieved to produce aggregated units. The size of the aggregated units was measured to determine the percentage falling between 200 μm and 500 μm. The friability of the first three batches of aggregate units was also measured according to the friability test as previously described. The results were acceptable if the aggregated units had a friability index between 10 and 60. The friability of the rest of the batches' aggregated units was acceptable if the aggregated units could be utilized in the device described in U.S. patent application Ser. No. 08/309,691, which has previously been incorporated by reference. The results of six different fine powder compositions are shown in Table 1 below.

TABLE 1

| Fine Powder Composition | Nonaqueous Solvent/ Amount Added (g/g) | Screen Type/ Hole Size | Extruded Material in the Proper Size Range | Friability |
|---|---|---|---|---|
| Mannitol with HSA | PFOB/2.0 | Standard Sieve Screen/355 μm | 92% | Acceptable |
| Mannitol with Insulin | PFD/3.8 | Laser Drilled/250 μm | 69% | Acceptable |
| Mannitol with HSA | PFD/2.2 | Laser Drilled/175 μm | 73% | Acceptable |
| Mannitol with HSA | Acetone/0.8 | Laser Drilled/355 μm | 12% | Acceptable |
| Mannitol with HSA | Methylene Chloride/1.3 | Laser Drilled/355 μm | 14% | Acceptable |
| Mannitol with HSA | Toluene/0.9 | Laser Drilled/355 μm | 64% | Acceptable |

Although the foregoing invention has been described in some detail by way of illustration and example, for purposes of clarity of understanding, it will be obvious that certain changes and modifications may be practiced within the scope of the appended claims.

What is claimed is:

1. A method for agglomerating fine particles, said method comprising;

combining a powder of fine particles with a binding liquid to produce a granulation or a paste;

dividing the granulation or paste into small volumes;

drying the small volumes to remove binding liquid and produce dry powder agglomerate units having a first size distribution; and adjusting the dry powder agglomerate units to have a second size distribution which is characterized by a friability index in the range from about 10 to 60.

2. A method as in claim 1, wherein the fine particles are characterized by a mean particle size in the range from 1 μm to 5 μm.

3. A method as in claim 1, wherein the dividing step comprises extruding the granulation or paste through a screen having holes in the range from 40 μm to 650 μm to divide the granulation or paste into small volumes.

4. A method as in claim 3, wherein the holes are circular in geometry, and wherein the granulation or paste is extruded into elongate cylindrical portions.

5. A method as in claim 1, wherein the granulation or paste is dried at a temperature in the range from 15° C. to 40° C.

6. A method as in claim 1, wherein the granulation or paste is dried in a vacuum.

7. A method as in claim 1, wherein the granulation or paste is dried by forced air convection.

8. A method as in claim 1, wherein the adjusting step comprises sieving the dry powder agglomerate units to adjust the dry powder agglomerate units to the second size distribution.

9. A method as in claim 8, wherein the dry powder agglomerate units are adjusted to have a second size distribution characterized by a mean size in the range from 50 μm to 600 μm.

10. A method as in claim 9, wherein the second size distribution is further characterized by a size distribution wherein at least 90% of the dry powder agglomerate units have a size within about ±250 μm of each other.

11. A method as in claim 1, further comprising treating the size adjusted agglomerate units to have a spherical geometry.

12. A method as in claim 11, wherein the treating step comprises rolling the agglomerate units in a container to spheronize the agglomerate units.

13. A method as in claim 1, wherein the binding liquid is a nonaqueous solvent, wherein the fine particles are a medicament powder, and wherein the amount of binding liquid added is based on the surface area of the fine particles.

14. A method as in claim 1, wherein the binding liquid is a fluorocarbon, wherein the fine particles have a mean particle size in the range from 1 μm to 5 μm, and wherein the amount of fluorocarbon added is in the range from 0.5 gram to 5 gram per gram of fine particles.

* * * * *